(12) United States Patent
Poinsard et al.

(10) Patent No.: US 9,505,720 B2
(45) Date of Patent: Nov. 29, 2016

(54) PHENOL DERIVATIVES AND PHARMACEUTICAL OR COSMETIC USE THEREOF

(71) Applicant: GALDERMA RESEARCH & DEVELOPMENT, Biot (FR)

(72) Inventors: Cédric Poinsard, Le Plan de Grasse (FR); Pascal Collette, Le Cannet (FR); Jean-Michel Linget, Benfeld (FR); Sandrine Rethore, Valbonne (FR); Pascale Mauvais, Antibes (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/707,711

(22) Filed: May 8, 2015

(65) Prior Publication Data

US 2016/0115132 A1   Apr. 28, 2016

Related U.S. Application Data

(63) Continuation of application No. 13/519,100, filed as application No. PCT/FR2010/052871 on Dec. 22, 2010, now Pat. No. 9,050,266.

(60) Provisional application No. 61/282,153, filed on Dec. 23, 2009.

(30) Foreign Application Priority Data

Dec. 23, 2009 (FR) .................... 09 59475

(51) Int. Cl.
| | |
|---|---|
| C07D 213/74 | (2006.01) |
| C07D 239/42 | (2006.01) |
| C07D 241/20 | (2006.01) |
| C07D 213/84 | (2006.01) |
| A61K 8/49 | (2006.01) |
| A61K 31/44 | (2006.01) |
| A61K 31/4965 | (2006.01) |
| A61K 31/499 | (2006.01) |
| A61K 31/505 | (2006.01) |
| A61Q 7/00 | (2006.01) |
| A61Q 19/00 | (2006.01) |
| A61K 8/69 | (2006.01) |
| A61Q 7/02 | (2006.01) |

(52) U.S. Cl.
CPC ............ *C07D 213/74* (2013.01); *A61K 8/494* (2013.01); *A61K 8/4926* (2013.01); *A61K 8/4953* (2013.01); *A61K 8/69* (2013.01); *A61K 31/44* (2013.01); *A61K 31/499* (2013.01); *A61K 31/4965* (2013.01); *A61K 31/505* (2013.01); *A61Q 7/00* (2013.01); *A61Q 7/02* (2013.01); *A61Q 19/00* (2013.01); *A61Q 19/008* (2013.01); *C07D 213/84* (2013.01); *C07D 239/42* (2013.01); *C07D 241/20* (2013.01)

(58) Field of Classification Search
USPC ........ 544/317, 326, 409, 408; 546/297, 312, 546/286, 294, 289
See application file for complete search history.

(56) References Cited

U.S. PATENT DOCUMENTS 4,578,390 A   3/1986   Jensen et al.

FOREIGN PATENT DOCUMENTS

| AU | 670942 B2 | 8/1996 |
| EP | 0580459 A1 | 1/1994 |
| WO | 2004/052868 A1 | 6/2004 |
| WO | 2005/042464 A1 | 5/2005 |

OTHER PUBLICATIONS

International Search Report dated Jun. 14, 2011 corresponding to International Patent Application No. PCT/FR2010/052871, and English language translation of the Search Report.

*Primary Examiner* — Kristin Vajda
(74) *Attorney, Agent, or Firm* — Dentons US LLP

(57) ABSTRACT

The present invention relates to novel compounds of general formula:

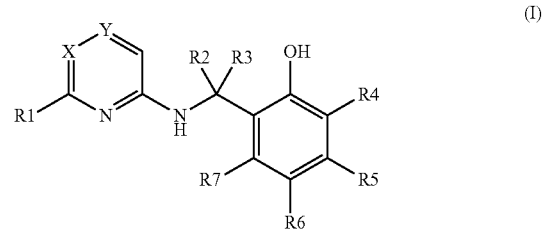

and to the cosmetic or pharmaceutical use thereof.

15 Claims, No Drawings

PHENOL DERIVATIVES AND PHARMACEUTICAL OR COSMETIC USE THEREOF

CROSS-REFERENCE TO PRIOR APPLICATIONS

This application is a continuation of U.S. patent application Ser. No. 13/519,100, filed Jul. 16, 2013, now issued as U.S. Pat. No. 9,050,266, which is a National Stage of PCT/FR2010/052871, filed Dec. 22, 2010, and designating the United States (published in French on Jun. 30, 2011, as WO 2011/077043 A2; the title and abstract were published in English), which claims priority of FR 0959475, filed Dec. 23, 2009, and U.S. Provisional Patent Application No. 61/282,153, filed Dec. 23, 2009, each hereby expressly incorporated by reference in its entirety and each assigned to the assignee hereof.

The present invention relates to novel compounds of general formula:

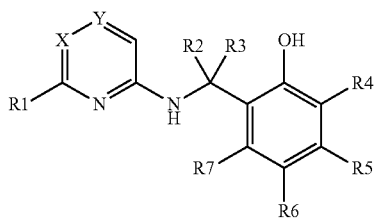

(I)

and to the cosmetic or pharmaceutical use thereof.

The present invention proposes to provide novel phenolic derivatives which are powerful androgen receptor modulators.

Among the prior art documents describing molecules which modulate androgen receptor activity, mention may, for example, be made of the phenylimidazolines described in patent application EP 580 459, or application WO 2005/42464.

The invention relates to novel phenolic derivatives that correspond to general formula (I) below:

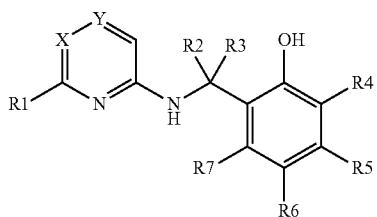

(I)

in which:

$R_1$ represents a $C_{2-6}$ alkyl, $C_{3-7}$ cycloalkyl, $C_{1-6}$ alkyloxy, —S(O)$_m$—$C_{1-6}$ alkyl, $C_{1-6}$ fluoroalkyl, $C_{1-6}$ fluoroalkyloxy, —(CH$_2$)$_n$—$C_{3-9}$ cycloalkyl, —(CH$_2$)$_n$—$C_{3-9}$ cycloalkyl, $C_{2-6}$ alkyl-OH, —(CH$_2$)$_n$—$C_{1-6}$ alkyloxy, —(CH$_2$)$_n$—$C_{1-6}$ fluoroalkyl, —(CH$_2$)$_p$—O—$C_{1-6}$ fluoroalkyl, COR$_a$, CN, NO$_2$ or NR$_8$R$_9$ group, a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different R$_b$ groups.

$R_2$ and $R_3$ are identical or different and represent a hydrogen atom or a $C_{1-9}$ alkyl, $C_{3-9}$ cycloalkyl, $C_{1-6}$ fluoroalkyl, —(CH$_2$)$_r$—$C_{3-9}$ cycloalkyl, —$C_{2-6}$ alkyl-OH, —(CH$_2$)$_r$—$C_{1-6}$ alkyloxy, —(CH$_2$)$_r$—$C_{3-7}$ cycloalkyl, —(CH$_2$)$_r$—$C_{1-6}$ fluoroalkyl, or —(CH$_2$)$_q$—O—$C_{1-6}$ fluoroalkyl group.

Optionally, the $R_2$ and $R_3$ groups can form, with the carbon atom which bears them, a $C_{3-9}$ cycloalkyl group or a heterocycle such as tetrahydrofuran, tetrahydropyran, tetrahydrothiopyran, tetrahydro-1-oxythiopyran or tetrahydro-1,1-dioxythiopyran.

$R_4$, $R_5$, $R_6$, $R_7$ are identical or different and represent either a hydrogen atom or a $C_{1-6}$ alkyl, $C_{3-7}$ cycloalkyl, $C_{1-6}$ alkyloxy, —S(O)$_s$—$C_{1-6}$ alkyl, $C_{1-6}$ fluoroalkyl, $C_{1-6}$ fluoroalkyloxy, —(CH$_2$)$_t$—$C_{3-9}$ cycloalkyl, —(CH$_2$)$_t$—$C_{3-9}$ cycloalkyl, —$C_{1-6}$ alkyl-OH, —(CH$_2$)$_t$C$_{1-6}$ alkyloxy, —(CH$_2$)$_t$—$C_{1-6}$ fluoroalkyl, —(CH$_2$)$_u$—O—$_{1-6}$ fluoroalkyl, COR$_d$, CN or NR$_8$R$_9$, group, or a halogen or a phenyl or heteroaryl group containing either a) from 1 to 4 nitrogen atoms or b) an oxygen or sulphur atom and 1 or 2 nitrogen atom(s). These phenyl and heteroaryl groups may be optionally substituted with one to three identical or different R$_c$ groups.

X represents CH or N.

Y represents either a nitrogen atom, or a carbon atom substituted with a $C_{1-6}$ alkyl, $C_{3-7}$ cycloalkyl, $C_{1-6}$ alkyloxy, —S(O)$_v$C$_{1-6}$ alkyl, $C_{1-6}$ fluoroalkyl, $C_{1-6}$ fluoroalkyloxy, —(CH$_2$)$_j$—$C_{3-9}$ cycloalkyl, —(CH$_2$)$_j$—$C_{3-9}$ cycloalkyl, $C_{1-6}$ alkyl-OH, —(CH$_2$)$_j$—$C_{1-6}$ alkyloxy, —(CH$_2$)$_j$—$C_{1-6}$ fluoroalkyl, —(CH$_2$)$_w$—O—$C_{1-6}$ fluoroalkyl, COR$_e$, CN, NR$_{10}$R$_{11}$ or NO$_2$ group, a hydrogen atom or a halogen or a phenyl or heteroaryl group containing either a) from 1 to 4 nitrogen atoms or b) an oxygen or sulphur atom and 1 or 2 nitrogen atom(s). These phenyl or heteroaryl groups may be optionally substituted with one to three identical or different Rb groups;

Ra, Rd and Re are identical or different and represent a C1-6 alkyl, C1-6 alkyloxy or NR12R13 group.

Rb and Rc are identical or different and represent a halogen, or a $C_{1-6}$ alkyl, $C_{3-7}$ cycloalkyl, $C_{1-6}$ alkyloxy, —S(O)$_j$—$C_{1-6}$ alkyl, $C_{1-6}$ fluoroalkyl, $C_{1-6}$ fluoroalkyloxy, —(CH$_2$)$_i$—$C_{3-7}$ cycloalkyl, —(CH$_2$)$_i$—$C_{3-7}$ cycloalkyl, $C_{1-6}$ alkyl-OH, —(CH$_2$)$_i$—$C_{1-6}$ alkyloxy, —(CH$_2$)$_i$—$C_{1-6}$ fluoroalkyl, —(CH$_2$)$_z$—O—$C_{1-6}$ fluoroalkyl, COR$_a$, CN or NR$_{14}$R$_{15}$ group.

$R_8$ and $R_8$' are identical or different and represent a $C_{1-6}$ alkyl, $C_{3-7}$ cycloalkyl, —(CH$_2$)$_f$—$C_{3-7}$ cycloalkyl or —(CH$_2$)$_f$—$C_{1-6}$ fluoroalkyl group.

$R_9$, $R_9$', $R_{10}$, $R_{11}$, $R_{12}$, $R_{13}$, $R_{14}$ and $R_{15}$ are identical or different and represent a a hydrogen atom or a $C_{1-6}$ alkyl, $C_{3-7}$ cycloalkyl, —(CH$_2$)$_g$—$C_{3-7}$ cycloalkyl or —(CH$_2$)$_g$—$C_{1-6}$ fluoroalkyl group.

Optionally, the $R_8$ and $R_9$ groups can form, with the nitrogen atom which bears them, a heterocycle such as: azetidine, pyrrolidine, piperidine, azepane, morpholine or piperazine. Optionally, the $R_8$' and $R_9$' groups can form, with the nitrogen atom which bears them, a heterocycle such as: azetidine, pyrrolidine, piperidine, azepane, morpholine or piperazine. Optionally, the $R_{10}$ and $R_{11}$ groups can form, with the nitrogen atom which bears them, a heterocycle such as: azetidine, pyrrolidine, piperidine, azepane, morpholine or piperazine. Optionally, the $R_{12}$ and $R_{13}$ groups can form, with the nitrogen atom which bears them, a heterocycle such as:

azetidine, pyrrolidine, piperidine, azepane, morpholine or piperazine. Optionally, the $R_{14}$ and $R_{15}$ groups can form, with the nitrogen atom which bears them, a heterocycle such as: azetidine, pyrrolidine, piperidine, azepane, morpholine or piperazine.

f, g, i, l, n, r and t are different or identical and are equal to 1, 2 or 3 j, m, s and v are different or identical and are equal to 0, 1 or 2 p, q, u, w and z are different or identical and are equal to 2, 3 or 4 and also the pharmaceutically acceptable salts, solvates or hydrates thereof and the conformers or rotamers thereof.

The compounds of formula (I) may comprise one or more asymmetric carbon atoms. They may thus exist in the form of a mixture of enantiomers or of diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention. These salts are advantageously prepared with pharmaceutically acceptable acids, but the salts of other acids that are useful, for example for purifying or isolating the compounds of formula (I), also form part of the invention. These acids may be, for example, picric acid, oxalic acid or an optically active acid, for example a tartaric acid, a dibenzoyltartaric acid, a mandelic acid or a camphorsulphonic acid, and those that form physiologically acceptable salts, such as hydrochloride, hydrobromide, sulphate, hydrogen sulphate, dihydrogen phosphate, maleate, fumarate, 2-naphthalenesulphonate or para-toluenesulphonate. For a review of physiologically acceptable salts, see the Handbook of Pharmaceutical Salts: Properties, Selection and Use by Stahl and Wermuth (Wiley-VCH, 2002).

The solvates or hydrates may be obtained directly after the synthesis process, compound (I) being isolated in the form of a hydrate, for example a monohydrate or hemihydrate, or of a solvate of the reaction or purification solvent.

In the context of the invention, the following definitions apply:

$C_{b-c}$ in which b and c may take values from 1 to 9: a carbon-based chain of b to c carbon atoms, for example $C_{1-6}$ is a carbon-based chain that may contain from 1 to 6 carbon atoms, alkyl: a linear or branched saturated aliphatic group, for example a $C_{1-6}$ alkyl group represents a linear or branched carbon-based chain of 1 to 6 carbon atoms, preferably a methyl, ethyl, propyl, isopropyl, butyl, isobutyl, tert-butyl, pentyl or hexyl group, cyloalkyl: a cyclic, optionally branched, saturated carbon-based chain containing from 3 to 7 carbon atoms. By way of example, a $C_{3-7}$ cycloalkyl group represents a carbon-based chain containing from 3 to 7 carbon atoms, preferably a cyclopropyl, cyclobutyl, cyclopentyl, cyclohexyl or cycloheptyl, heterocycle: a cyclic or bicyclic, saturated or unsaturated hydrocarbon-based chain comprising one or more heteroatoms chosen from O, S and N, heteroaryl: an aromatic heterocycle, preferably a pyridinyl, pyrazinyl, pyrimidinyl, pyridazinyl, triazinyl, pyrazolyl, isooxazolyl, oxadiazolyl, thiazolyl, thiadiazolyl, triazolyl or imidazolyl group, halogen: a fluorine, chlorine or bromine atom, alkyloxy: an —O-alkyl group, alkylthio: an —S-alkyl group, fluoroalkyl: an alkyl group in which one or more hydrogen atoms have been replaced with a fluorine atom, fluoroalkyloxy: an alkyloxy group in which one or more hydrogen atoms have been replaced with a fluorine atom.

The group (A) of the compounds of formula (I) defined above is preferred, in which compounds:

X represents CH and Y represents a carbon atom substituted by one of the groups as defined above and preferably a methyl, ethyl, isopropyl, cyclopropyl, $CF_3$, $CONH_2$, $CO_2CH_3$, $CO_2CH_2CH_3$, CN, $NO_2$, $SCH_3$ or $SCH_2CH_3$ group, a hydrogen atom, a halogen or a $OCF_3$, $OCH_3$, $OCH_2CH_3$ or $OCH(CH_3)_2$ group.

The group (B) of the compounds of formula (I), the substituents X and Y of which are defined above or in the preferred group (A) and such that the group $R_1$ represents a halogen, an ethyl, isopropyl, trifluoromethyl, nitrile, nitro, methoxy, ethoxy, isopropoxy, thiomethyl, thioethyl or thioisopropyl group, is a group of preferred compounds and more particularly such that $R_1$ represents a halogen or a methoxy, ethoxy, thiomethyl, thioethyl or trifluoromethyl group.

The compounds below, and the pharmaceutically acceptable salts, solvates and hydrates, and the conformers or rotamers thereof, are particularly preferred:

2-[(6-Methoxypyridin-2-ylamino)methyl]phenol
2-[(6-Bromopyridin-2-ylamino)methyl]phenol
2-[(6-Bromopyridin-2-ylamino)methyl]-4-fluorophenol
6-(2-Hydroxybenzylamino)pyridine-2-carbonitrile
2-[1-(6-Methoxypyridin-2-ylamino)ethyl]phenol
2-[(6-Trifluoromethylpyridin-2-ylamino)methyl]phenol
2-[(6-Chloropyridin-2-ylamino)methyl]phenol
2-[(6-Ethylpyridin-2-ylamino)methyl]phenol
2-[(6-Ethoxypyridin-2-ylamino)methyl]phenol
2-[(6-Isopropoxypyridin-2-ylamino)methyl]phenol
5-Chloro-2-[(6-methoxypyridin-2-ylamino)methyl]phenol
2-[(2-Trifluoromethylpyrimidin-4-ylamino)methyl]phenol
2-[(6-Bromopyrazin-2-ylamino)methyl]phenol
2-[(2-Chloropyrimidin-4-ylamino)methyl]phenol
2-[(2-Bromopyrimidin-4-ylamino)methyl]phenol
2-[(2-Chloro-6-methylpyrimidin-4-ylamino)methyl]phenol
2-[(6-Chloro-4-trifluoromethylpyridin-2-ylamino)methyl]phenol
2-[(6-Chloro-4-methylpyridin-2-ylamino)methyl]phenol
2-[(6-Methoxypyrazin-2-ylamino)methyl]phenol
2-[(2-Methoxypyrimidin-4-ylamino)methyl]phenol
2-[(2-Methoxy-6-methylpyrimidin-4-ylamino)methyl]phenol
2-[(6-Methylsulphanylpyridin-2-ylamino)methyl]phenol
2-[(6-Methanesulphinylpyridin-2-ylamino)methyl]phenol
2-[(6-Methanesulphonylpyridin-2-ylamino)methyl]phenol
2-[(6-Methoxypyridin-2-ylamino)methyl]-6-methylphenol
2-[(4-Bromo-6-methoxypyridin-2-ylamino)methyl]phenol
2-[(6-Bromo-2-methoxypyrimidin-4-ylamino)methyl]phenol
2-[(4-Chloro-6-methoxypyridin-2-ylamino)methyl]phenol
2-[(6-Bromo-2-methoxypyrimidin-4-ylamino)methyl]phenol
2-[(4-Bromo-6-methoxypyridin-2-ylamino)methyl]-6-fluorophenol
2-[(4-Bromo-6-methoxypyridin-2-ylamino)methyl]-5-fluorophenol
2-[(4-Bromo-6-methoxypyridin-2-ylamino)methyl]-3-fluorophenol
2-[(4-Bromo-6-methoxypyridin-2-ylamino)methyl]-4-fluorophenol 2-[(6-Bromo-2-methoxypyrimidin-4-ylamino)methyl]-4-fluorophenol
2-[(4-Chloro-6-methoxypyridin-2-ylamino)methyl]-4-fluorophenol
2-[(6-Chloro-2-methoxypyrimidin-4-ylamino)methyl]-4-fluorophenol
2-[1-(4-Bromo-6-methoxypyridin-2-ylamino)ethyl]phenol
2-[1-(4-Bromo-6-methoxypyridin-2-ylamino)propyl]phenol
2-[1-(6-Bromo-4-methylpyridin-2-ylamino)-1-methylethyl]phenol
2-[1-(4-Bromo-6-methoxypyridin-2-ylamino)propyl]-4-fluorophenol
2-[1-(6-Bromopyridin-2-ylamino)propyl]-4-fluorophenol
4-Fluoro-2-[(6-methoxypyridin-2-ylamino)methyl]phenol
4-Fluoro-2-[(6-methoxypyridin-2-ylamino)ethyl]phenol
4-Fluoro-2-[(6-methoxypyridin-2-ylamino)propyl]phenol
2-[(6-Bromo-4-methoxypyridin-2-ylamino)methyl]phenol
2-[(6-Bromo-4-methylpyridin-2-ylamino)methyl]phenol
2-[(6-Chloro-4-methoxypyridin-2-ylamino)methyl]phenol A subject of the invention is also a process for preparing the compounds of general formula (I).

In accordance with the invention, the compounds of formula (I) can be prepared by one of the three methods described in Scheme 1 below and optionally completed by one or more of the reactions as described in Scheme 2.

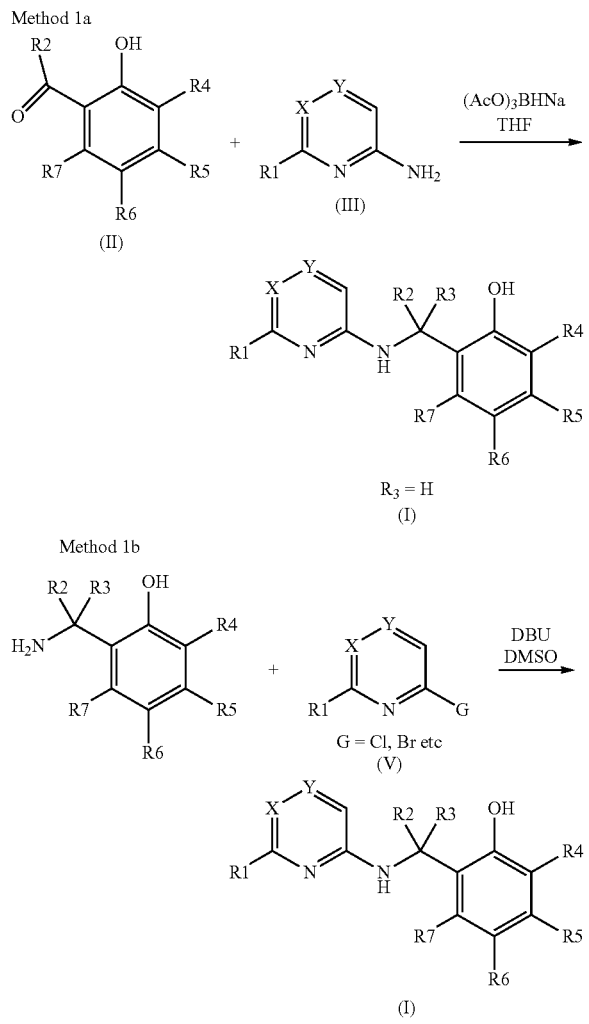

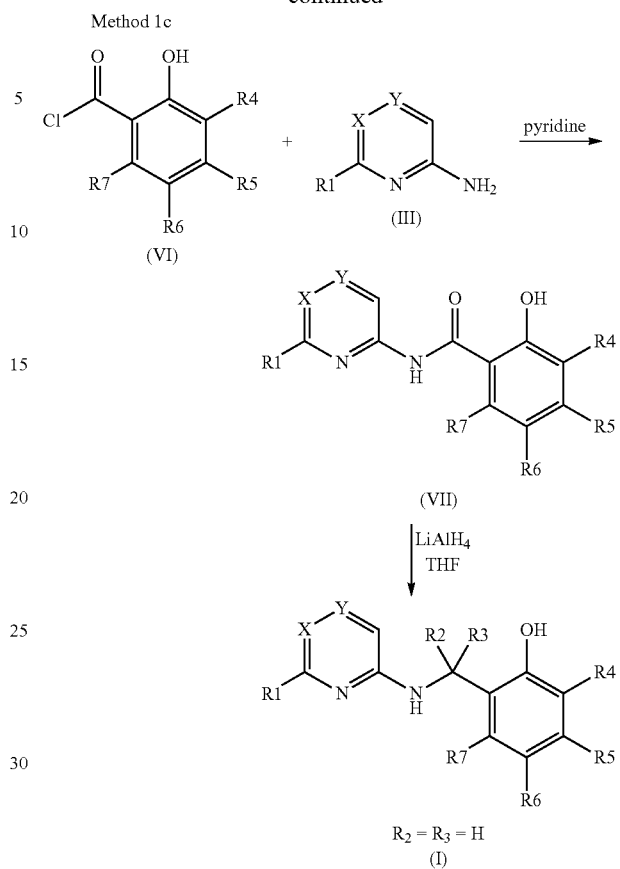

The phenolic compounds of formula (I) in which $R_1$, $R_2$, $R_3$, $R_4$, $R_5$, $R_6$, $R_7$, X and Y are as defined above can be prepared by means of a reductive amination reaction between an aldehyde or a benzyl ketone (II) and an amine (III) in the presence of a reducing agent, such as, for example, and in a non-limiting manner, sodium triacetoxyborohydride, according to Method 1a illustrated in Scheme 1 and by analogy, for example, with the reactions described in Org. Pro. R. & D. (2006) 971-1031.

The phenolic compounds of formula (I) can be prepared by reaction between heterocycles (V) comprising a leaving group and benzyl amines in the presence of a base such as, in a non-limiting manner, 1,8-diazabicyclo[5.4.0]undec-7-ene, for example in a solvent such as dimethyl sulphoxide and as described by Method 1b of Scheme 1. The term "leaving group" denotes a group well known to those skilled in the art, such as, in a non-limiting manner, a halogen, a mesylate, a tosylate or a triflate.

The third method of preparing phenolic compounds of formula (I) consists in reducing amide intermediates (VII) using a reactive hydrogen donor such as, in a non-limiting manner, lithium aluminium hydride as illustrated by Method 1c of Scheme 1. These amide intermediates may be prepared by reaction between, for example, and in a non-limiting manner, an acyl chloride (VI) and an amine (III) in pyridine. The acyl chlorides (VI) are prepared from the acids according to techniques well known to those skilled in the art, for example at reflux in thionyl chloride.

Certain compounds comprising a sulphoxy group (X) or sulphone group (XI) may optionally be prepared by oxidation of the thioether intermediate (IX) as described in Scheme 2 according to Method 2a. The oxidation may for example, and in a non-limiting manner, be carried out by oxone. The thioether intermediate (IX) may be prepared from compounds (VIII) comprising a leaving group such as, in a non-limiting manner, a chlorine atom, by reaction with a thiolate in dimethyl sulphoxide. Certain compounds comprising an ether group may optionally be prepared by reaction of the intermediate (VIII) with the corresponding alcohol such as, for example, and in a non-limiting manner, methanol in the presence of a base such as sodium hydroxide, optionally by heating in a microwave oven and as described in Scheme 2 according to Method 2b.

The products which are subjects of the present invention have advantageous pharmacological properties; it was in particular noted that they modulate androgen receptor activity.

Tests given in the experimental section illustrate this androgen receptor-modulating activity. The products which are subjects of the present invention exhibit partial or total antagonist or agonist activities. Because of this activity, the products of the invention can be used as medicaments in humans or animals.

These properties make the products of general formula (I) of the present invention usable as medicaments for treating

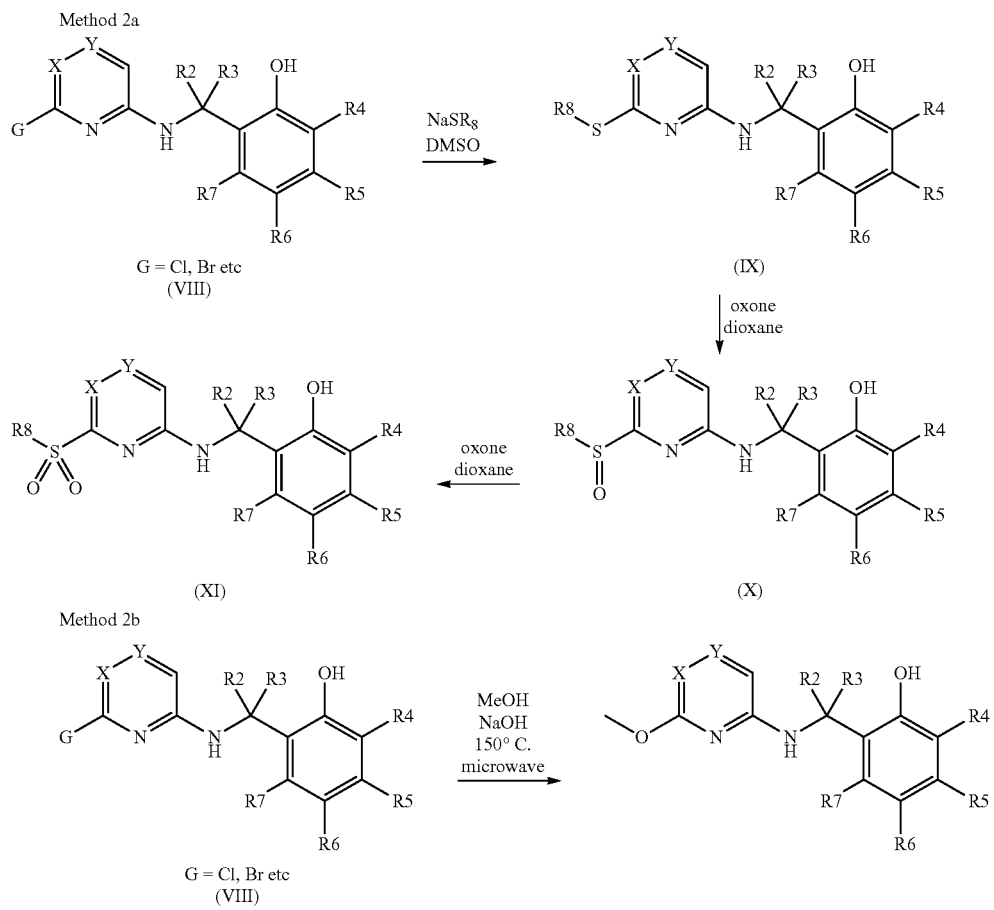

The functional groups optionally present in the reaction intermediates used in the process may be protected, either permanently or temporarily, with protecting groups that ensure an unequivocal synthesis of the expected compounds. The protection and deprotection reactions are performed according to techniques that are well known to those skilled in the art. The term "temporary protecting group for amines, alcohols or carboxylic acids" means protecting groups such as those described in "Protective Groups in Organic Chemistry", edited by McOmie J. W. F., Plenum Press, 1973, in "Protective Groups in Organic Synthesis", 2nd edition, Greene T. W. and Wuts P. G. M., published by John Wiley & Sons, 1991, and in "Protecting Groups", Kocienski P. J., 1994, Georg Thieme Verlag.

hormone-dependent cancers such as prostate cancer or breast cancer, and also for combating benign prostatic hyperplasia, early puberty, virilization, polycystic ovary syndrome, Stein-Leventhal syndrome, loss of libido, or endometriosis. The compounds exhibiting partial or total agonist activity can in particular be used for treating afflictions such as loss of muscle mass (sarcopenia), muscle atrophy, impotence and male sterility, abnormal male differentiation (hermaphroditism), hypogonadism or osteoporosis. The products of general formula (I) of the invention find a cosmetic use in a compound for body or hair hygiene.

The products of general formula (I) of the invention also find a use in the treatment of hirsutism, acne, seborrhoea, oily skin, androgenic alopecia or hyperpilosity, and they can be used for the production of a medicament for preventing and/or treating hirsutism, androgenic alopecia, hyperpilosity, atopic dermatitis, or sebaceous gland disorders such as hyperseborrhoea, acne, oily skin or seborrhoeic dermatitis. The products of formula (I) can therefore be used in dermatology: they can be used alone or in combination. They can be combined in particular with an antibiotic product, such as derivatives of azelaic acid, fusidic acid or erythromycin, or with a retinoid derivative such as tretinoin for the treatment of acne, or with a 5a-reductase inhibitor such as (5alpha, 17beta)-N-1,1-dimethylethyl-3-oxo-4-azaandrost-1-ene-17-carboxamide (or Finasteride, Merck, 13th Edition) or azelaic acid or an androgen receptor-blocking agent for the treatment of acne, alopecia or hirsutism, or with a product that stimulates hair growth, such as Minoxidil, for the treatment of alopecia.

A subject of the present invention is also, as medicament, the compounds of formula (I) as described above, and also the pharmaceutically acceptable salts and pharmaceutically acceptable solvates and/or hydrates thereof.

Several examples of preparation of active compounds of formula (I) according to the invention, and the results of the biological activity of such compounds, are given hereinbelow as illustrations and with no limiting nature.

PROCEDURES

Example 1

2-[(6-Methoxypyridin-2-ylamino)methyl]phenol

Synthesis According to Scheme 1, Method 1a 512 mg (2.41 mmol, 1.5 eq) of sodium triacetoxyborohydride are added to a solution of 200 mg (1.61 mmol, 1 eq) of 6-methoxypyridin-2-ylamine (starting material 1) and 236 mg (2.41 mmol, 1 eq) of 2-hydroxybenzaldehyde (starting material 2) in 20 ml of tetrahydrofuran. The solution is stirred at room temperature for 48 h. It is evaporated and the residue is taken up in 100 ml of dichloromethane and then extracted with a saturated aqueous solution of ammonium chloride. The aqueous phase is extracted twice with dichloromethane. The organic phases are combined and dried over sodium sulphate. The residue is chromatographed on silica gel (5/95 ethyl acetate/heptane). 2-[(6-methoxypyridin-2-ylamino)methyl]phenol is obtained in the form of a white solid. Melting point=103° C.

$^1$H NMR (CDCl$_3$): 3.94 (s, 3H); 4.52 (d, 2H, J=3.08 Hz); 4.95 (s, 1H), 6.03 (dd, 2H, J=6.2 Hz, J'=1.64 Hz); 6.85 (t, 1H, J=6.28 Hz, J'=7.4 Hz); 6.95 (d, 1H, J=9.04 Hz); 7.15-7.23 (m, 2H); 7.36 (t, 1H, J=7.92 Hz, J'=7.96 Hz); 10.21 (s, 1H)

Preparation of the 6-aminopyridine-2-carbonitrile intermediate 340 mg (2.89 mmol, 1 eq) of zinc cyanide are added to 500 mg (2.89 mmol, 1 eq) of 6-bromopyridin-2-ylamine in 10 ml of dimethylformamide in a microwave tube. 170 mg (0.147 mmol, 0.05 eq) of tetrakis(triphenylphosphine)palladium are added. The medium is heated at 170° C. for 1 hour 30 minutes in a microwave oven. 50 ml of ethyl acetate are added to the medium, which is filtered over celite. The filtrate is washed with water and extracted with ethyl acetate. The organic phases are combined and dried over sodium sulphate. The residue is triturated in heptane. 6-Aminopyridine-2-carbonitrile is obtained in the form of an orange solid.

Melting point=92° C.

Preparation of the 6-ethoxypyridin-2-ylamine intermediate

Introduced into a microwave tube are 500 mg (2.89 mmol) of 2-amino-6-bromopyridine, to which 2 ml of ethanol and 231 mg (5.78 mmol, 2 eq) of sodium hydroxide are added. The mixture is heated for 10 hours in a microwave oven at 170° C. The reaction medium is diluted with 50 ml of dichloromethane and then washed twice with 50 ml of water. The organic phase is concentrated to dryness and the residue is purified by chromatography over silica with, as eluent, heptane/ethyl acetate (1/1). The expected product is obtained in the form of a colourless oil.

Preparation of the 6-isopropoxypyridin-2-ylamine intermediate

This intermediate is prepared according to the procedure described for 6-ethoxypyridin-2-ylamine, replacing the ethanol with isopropanol. The expected product is obtained in the form of a colourless oil.

Examples 2 to 12

Examples 2 and 12 are described in Table 1 below. The compounds are synthesized according to the procedure described above, replacing the starting materials 1 and 2 mentioned in Example 1 with the products mentioned in Table 1.

TABLE 1

| Example # | IUPAC name | Starting material 1 | Starting material 2 | Melting point (° C.) | $^1$H NMR - 400 MHz (s = singlet, d = doublet, t = triplet, m = multiplet, q = quartet, J = coupling constant in Hz) |
|---|---|---|---|---|---|
| 2 | 2-[(6-bromo-pyridin-2-ylamino)-methyl]-phenol | 2-bromo-pyridin-6-ylamine | 2-hydroxy-benzaldehyde | 127 | (CDCl$_3$) 4.48 (d, 2H, J = 4.28 Hz); 5.17 (s, 1H); 6.35 (d, 1H, J = 8.7 Hz); 6.77 (d, 1H, J = 7.3 Hz); 6.87 (t, 1H, J = 7.4 Hz); 7.0 (d, 1H, J = 9.1 Hz); 7.16-7.27 (m, 3H); 9.84 (s, 1H) |
| 3 | 2-[(6-bromo-pyridin-2-yl-amino)-methyl]-4-fluoro- | 6-bromo-pyridin-2-ylamine | 5-fluoro-2-hydroxy-benzaldehyde | 143 | (DMSO) 4.32 (d, 2H, J = 6 Hz); 6.5 (d, 1H, J = 8.2 Hz); 6.65 (d, 1H, J = 7.4 Hz); 6.77-6.81 (m, 1H); 6.85-6.95 (m, 2H); 7.3 (t, 1H, J = 8.2 Hz); 7.32-7.35 (m, 1H); |

TABLE 1-continued

| Example # | IUPAC name | Starting material 1 | Starting material 2 | Melting point (° C.) | ¹H NMR - 400 MHz (s = singlet, d = doublet, t = triplet, m = multiplet, q = quartet, J = coupling constant in Hz) |
|---|---|---|---|---|---|
| | phenol | | | | 9.59 (s, 1H) |
| 4 | 6-(2-hydroxy-benzyl-amino)-pyridine-2-carbonitrile | 6-amino-pyridine-2-carbonitrile | 2-hydroxy-benzaldehyde | 153 | (DMSO) 4.36 (d, 2H, J = 4.8 Hz); 6.73 (t, 1H, J = 7.4 Hz); 6.81-6.84 (m, 2H); 7.04-7.08 (m, 2H); 7.14 (d, 1H, J = 7.4 Hz); 7.46-7.54 (m, 2H); 9.60 (s, 1H) |
| 5 | 2-[1-(6-methoxy-pyridin-2-yl-amino)-ethyl]-phenol | 6-methoxy-pyridin-2-ylamine | 1-(2-hydroxy-phenyl)-ethanone | 109 | (DMSO) 1.35 (d, 3H, J = 6.8 Hz); 3.66 (s, 3H); 5.13-5.16 (m, 1H); 5.79 (d, 1H, J = 7.7 Hz); 5.94 (d, 1H, J = 7.8 Hz); 6.7 (t, 1H, J = 7.3 Hz); 6.77 (t, 2H, J = 8.2 Hz); 6.97 (t, 1H, J = 7.6 Hz); 7.20-7.24 (m, 2H); 9.42 (s, 1H) |
| 6 | 2-[(6-trifluoro-methyl-pyridin-2-yl-amino)-methyl]-phenol | 2-amino-6-(trifluoro-methyl)-pyridine | 2-hydroxy-benzaldehyde | 125 | (DMSO) 4.38 (d, 2H, J = 5.4 Hz); 6.71-6.82 (m, 3H); 6.88 (d, 1H, J = 7.2 Hz); 7.06 (t, 1H, J = 7.6 Hz); 7.19 (d, 1H, J = 7.4 Hz); 7.37-7.40 (m, 1H); 7.56 (t, 1H, J = 7.8 Hz); 9.56 (s, 1H) |
| 7 | 2-[(6-chloro-pyridin-2-yl-amino)-methyl]-phenol | 2-amino-6-chloro-pyridine | 2-hydroxy-benzaldehyde | not determined | (DMSO) 4.34 (d, 1H, J = 5.8 Hz); 6.45-6.50 (m, 2H); 6.72-6.76 (m, 2H) 6.81 (d, 1H, J = 8 Hz); 7.06 (t, 1H, J = 7.6 Hz); 7.15 (d, 1H, J = 7.4 Hz); 7.26-7.29 (m, 1H); 7.38 (t, 1H, J = 7.5 Hz); 9.57 (s, 1H) |
| 8 | 2-[(6-ethyl-pyridin-2-yl-amino)-methyl]-phenol | 6-ethyl-pyridin-2-ylamine | 2-hydroxy-benzaldehyde | not determined | (DMSO) 1.2 (t, 3H, J = 7.6 Hz); 2.54-2.60 (q, 2H, J = 7.5 Hz); 4.31 (d, 2H, J = 6.12 Hz); 6.33-6.38 (m, 2H); 6.72-6.78 (m, 2H); 7.06-7.12 (m, 2H); 7.18 (d, 1H, J = 7.4 Hz); 7.3 (t, 1H, J = 7.5 Hz); 10.88 (s, 1H) |
| 9 | 2-[(6-ethoxy-pyridin-2-yl-amino)-methyl]-phenol | 2-amino-6-ethoxy-pyridine | 2-hydroxy-benzaldehyde | 87 | (CD₃OD) 1.35 (t, 3H, J = 7.0 Hz); 3.31-3.33 (q, 2H, J = 7.0 Hz); 4.42 (s, 2H); 5.91-5.93 (m, 1H); 6.05 (d, 1H, J = 7.8 Hz); 6.75-6.80 (m, 2H); 7.05-7.10 (m, 1H); 7.19-7.22 (m, 1H); 7.29-7.33 (m, 1H) |
| 10 | 2-[(6-isopropoxy-pyridin-2-yl-amino)-methyl]-phenol | 2-amino-6-isopropoxy-pyridine | 2-hydroxy-benzaldehyde | not determined | (CD₃OD) 1.26 (t, 6H, J = 6.1 Hz); 4.43 (s, 2H); 5.03-5.09 (m, 1H); 5.88-5.90 (m, 1H); 6.02-6.04 (m, 1H); 6.74-6.79 (m, 2H); 7.04-7.08 (m, 1H); 7.19-7.21 (m, 1H); 7.3 (t, 1H, J = 7.9 Hz) |
| 11 | 5-chloro-2-[(6-methoxy-pyridin-2-yl-amino)-methyl]-phenol | 6-methoxy-pyridin-2-ylamine | 4-chloro-2-hydroxy-benzaldehyde | not determined | (DMSO) 3.72 (s, 3H); 4.39 (d, 2H, J = 5.9 Hz); 5.86 (d, 1H, J = 7.8 Hz); 6.03 (d, 1H, J = 7.9 Hz); 6.7 (m, 1H); 6.8 (s, 1H); 6.93 (m, 1H); 7.21 (d, 1H, J = 8.4 Hz); 7.28 (t, 1H, J = 7.8 Hz); 9.73 (s, 1H) |
| 12 | 2-[(2-trifluoro-methyl-pyrimidin-4-ylamino)-methyl]-phenol | 2-trifluoro-methyl-pyrimidin-4-ylamine | 2-hydroxy-benzaldehyde | 201 | (DMSO) 4.34-4.47 (m, 2H); 6.55-6.85 (m, 3H); 7.1 (t, 1H, J = 7.4 Hz); 7.19 (d, 1H, J = 7.3 Hz); 8.15 (d, 1H, J = 5.9 Hz); 8.39-8.47 (m, 1H); 9.63 (s, 1H) |

Example 13

2-[(6-Bromopyrazin-2-ylamino)methyl]phenol

Synthesis According to Scheme 1, Method 1b

Introduced into a 50 ml round-bottomed flask is 1 g (4.2 mmol) of 2,6-dibromopyrazine (starting material 3), to which 15 ml of dimethyl sulphoxide, 638 mg (4.2 mmol, 1eq) of 1,8-diazabicyclo[5.4.0]undec-7-ene, and 1.03 g (8.4 mmol, 2 eq) of 2-hydroxybenzylamine (starting material 4) are added; the mixture is left stirring for 2 h at room temperature. The reaction medium is diluted with 50 ml of ethyl acetate and then the mixture is washed with 50 ml of a saturated solution of ammonium chloride, and then twice with 50 ml of water. The organic phases are dried over magnesium sulphate, filtered and concentrated to dryness. The residue is purified by chromatography over silica with, as eluent, a heptane/ethyl acetate (8/2) mixture. 2-[(6-Bromopyrazin-2-ylamino)methyl]phenol is obtained in the form of a white solid.

Melting point=168° C.

$^1$H NMR (DMSO): 4.36 (d, 1H, J=5.3 Hz); 6.74-6.76 (m, 1H); 6.83 (dd, 1H); 7.07-7.11 (m, 1H); 7.17 (dd, 1H); 7.75 (s, 1H); 7.80-7.83 (m, 1H); 7.96 (s, 1H); 9.61 (s, 1H)

Examples 14 to 18

Examples 14 to 18 are described in Table 2 below. The compounds are synthesized according to the procedure described above, replacing the starting materials 3 and 4 mentioned in Example 13 with the products mentioned in Table 2.

TABLE 2

| Example # | IUPAC name | Starting material 3 | Starting material 4 | Melting point (° C.) | $^1$H NMR - 400 MHz (s = singlet, d = doublet, t = triplet, m = multiplet, q = quartet, J = coupling constant in Hz) |
|---|---|---|---|---|---|
| 14 | 2-[(2-chloro-pyrimidin-4-ylamino)-methyl]-phenol | 2,4-dichloro-pyrimidine | 2-hydroxy-benzyl-amine | not determined | (CD$_3$OD) 4.53 (m, 2H); 6.45 (d, 1H, J = 6.0 Hz); 6.78-6.83 (m, 2H); 7.10-7.14 (m, 1H); 7.22 (d, 1H, J = 6.9 Hz); 7.83 (m, 1H) |
| 15 | 2-[(2-bromo-pyrimidin-4-ylamino)-methyl]-phenol | 2,4-dibromo-pyrimidine | 2-hydroxy-benzyl-amine | not determined | (CD$_3$OD) 4.42-4.52 (m, 2H); 6.48 (d, 1H, J = 6.0 Hz); 6.78-6.83 (m, 2H); 7.12 (t, 1H, J = 8.2 Hz); 7.21-7.23 (m, 1H); 7.76-7.86 (m, 1H) |
| 16 | 2-[(2-chloro-6-methyl-pyrimidin-4-ylamino)-methyl]-phenol | 2,4-dichloro-6-methyl-pyrimidine | 2-hydroxy-benzyl-amine | not determined | (DMSO) 2.17 (s, 3H); 4.40 (s, 2H); 6.35 (s, 1H); 6.74 (t, 1H, J = 7.4 Hz); 6.82 (d, 1H, J = 7.9 Hz); 7.06-7.12 (m, 2H); 8.04 (s, 1H); 9.60 (s, 1H). |
| 17 | 2-[(6-chloro-4-trifluoro-methyl-pyridin-2-ylamino)-methyl]-phenol | 2,6-dichloro-4-trifluoro-methyl-pyridine | 2-hydroxy-benzyl-amine | not determined | (DMSO) 4.39 (d, 2H, J = 5.4 Hz); 6.73-6.84 (m, 4H); 7.080 (t, 1H, J = 7.6 Hz); 7.17 (d, 1H, J = 7.4 Hz); 7.83 (s, 1H); 9.61 (s, 1H) |
| 18 | 2-[(6-chloro-4-methyl-pyridin-2-ylamino)-methyl]-phenol | 2,6-dichloro-4-methyl-pyridine | 2-hydroxy-benzyl-amine | 138 | (DMSO) 2.12 (s, 3H); 4.32 (d, 2H, J = 5.5 Hz); 6.28 (s, 1H); 6.37 (s, 1H); 6.73 (t, 1H, J = 7.4 Hz); 6.8 (d, 1H, J = 8 Hz); 7.04 (t, 1H, 7.7 Hz); 7.12-7.17 (m, 2H); 9.58 (s, 1H) |

Example 19

2-[(6-Methoxypyrazin-2-ylamino)methyl]phenol

Synthesis According to Scheme 2, Method 2b

Introduced into a microwave tube are 363 mg (1.29 mmol) of 2-[(6-bromopyrazin-2-ylamino)methyl]phenol, prepared as described previously in Example 12, to which 3 ml of methanol and 103 mg (2.58 mmol, 2 eq) of sodium hydroxide are added. The reaction mixture is then heated for 30 mins in a microwave oven at 150° C. and is then diluted with 50 ml of ethyl acetate. The mixture is neutralized with an ammonium chloride solution to pH=7, decanted and the organic phase is washed twice with 50 ml of water. The organic phase is dried over magnesium sulphate, filtered, and concentrated to dryness. The residue is purified by chromatography over silica with, as eluent, heptane/ethyl acetate (7/3). 2-[(6-Methoxypyrazin-2-ylamino)methyl]phenol is obtained in the form of a white solid.

Melting point=158° C.

$^1$H NMR (DMSO): 3.78 (s, 1H); 4.40 (d, 2H, J=5.2 Hz); 6.73 (t, 1H, J=7.4 Hz); 6.81 (d, 1H, J=8 Hz); 7.05 (t, 1H,

J=7.8 Hz); 7.19 (d, 1H, J=7.4 Hz); 7.26 (s, 1H); 7.31-7.32 (m, 1H); 7.50 (s, 1H); 9.55 (s, 1H).

Example 20

2-[(2-Methoxypyrimidin-4-ylamino)methyl]phenol

This compound is prepared according to the procedure described for Example 19, starting from 2-[(2-chloropyrimidin-4-ylamino)methyl]phenol. 2-[(2-Methoxypyrimidin-4-ylamino)methyl]phenol is obtained in the form of a white solid.

Melting point=161° C.
$^1$H NMR (CD$_3$OD): 3.90 (s, 3H); 4.53 (s, 3H); 6.15 (d, 2H, J=6.0 Hz); 6.77-6.81 (m, 2H); 7.07-7.12 (m, 1H); 7.21 (d, 1H, J=7.4 Hz); 7.78 (s, 1H)

Example 21

2-[(2-Methoxy-6-methylpyrimidin-4-ylamino)methyl]phenol

This compound is prepared according to the procedure described for Example 19 above, starting from 2-[(2-chloro-6-methylpyrimidin-4-ylamino)methyl]phenol.
$^1$H NMR (DMSO): 2.12 (s, 3H); 3.74 (s, 3H); 4.38 (m, 2H); 6.04 (s, 1H); 6.73 (t, 1H, J=7.4 Hz); 6.80 (d, 1H, J=8.0 Hz); 7.06 (t, 1H, J=7.7 Hz); 7.11 (d, 1H, J=7.3 Hz); 7.65 (s, 1H); 9.71 (s, 1H).

Example 22

2-[(6-Methylsulphanylpyridin-2-ylamino)methyl]phenol

Synthesis According to Scheme 2, Method 2a

Introduced into a microwave tube are 300 mg (1.28 mmol) of 2-[(6-chloropyridin-2-ylamino)methyl]phenol, to which 5 ml of dimethyl sulphoxide and 448 mg (6.4 mmol, 5 eq) of sodium methanethiolate are added. The reaction mixture is heated for 16 h at 90° C. The reaction medium is diluted with 50 ml of ethyl acetate and then washed with 50 ml of a saturated ammonium chloride solution then 2×50 ml of distilled water. The organic phase is dried over magnesium sulphate then filtered and concentrated to dryness. The residue is purified by chromatography over 40 g of silica with, as eluent, heptane/ethyl acetate (7/3). The product obtained is put back into solution in ethyl acetate, heptane is added until the solution becomes cloudy, it is then cooled to 0° C. and filtered. 2-[(6-Methylsulphanylpyridin-2-ylamino)methyl]phenol is obtained in the form of a white solid.

Melting point=61° C.
$^1$H NMR (DMSO): 2.38 (s, 3H); 4.38 (d, 2H, J=5.6 Hz); 6.21 (d, 1H, J=8.2 Hz); 6.34 (d, 1H,
J=7.4 Hz); 6.72 (t, 1H, 7.3 Hz); 6.93-6.96 (m, 1H); 7.04 (t, 1H, J=7.7 Hz); 7.15 (d, 1H, J=7.1 Hz); 7.23 (t, 1H, J=7.6 Hz); 9.65 (s, 1H).

Example 23

2-[(6-Methanesulphinylpyridin-2-ylamino)methyl]phenol 160 mg (0.66 mmol) of 2-[(6-methanesulphanylpyridin-2-ylamino)methyl]phenol and 406 mg (0.66 mmol, 1 eq) of oxone are mixed in 20 ml of dioxane. After stirring for one hour at room temperature, the reaction medium is heated at 90° C. for 4 h. After returning to room temperature, the reaction medium is diluted with 50 ml of ethyl acetate and then washed twice with 50 ml of water. The organic phase is dried over magnesium sulphate, filtered and concentrated to dryness. The residue is purified by chromatography over silica, eluting with a heptane/ethyl acetate (1/1) mixture. 2-[(6-Methanesulphinylpyridin-2-ylamino)methyl]phenol is obtained in the form of a white solid.

Melting point=133° C.
$^1$H NMR (CDCl$_3$): 2.89 (s, 3H); 4.51 (d, 2H, J=6.2 Hz); 5.32-5.33 (m, 1H); 6.5 (dd, 1H); 6.87-6.95 (m, 2H); 7.19-7.28 (m, 2H); 7.30-7.59 (m, 1H); 7.62 (t, 1H, J=7.3 Hz); 9.28 (s, 1H).

Example 24

2-[(6-Methanesulphonylpyridin-2-ylamino)methyl]phenol 80 mg (0.33 mmol) of 2-[(6-methanesulphanylpyridin-2-ylamino)methyl]phenol and 406 mg (0.66 mmol, 2 eq) of oxone are mixed in 20 ml of dioxane and heated for 16 h at 90° C. The reaction medium is diluted with 50 ml of ethyl acetate and then washed twice with 50 ml of water. The organic phase is dried over magnesium sulphate, filtered and concentrated to dryness. The residue is purified by chromatography over silica, eluting with a heptane/AcOEt (1/1) mixture. 2-[(6-Methanesulphonylpyridin-2-ylamino)methyl]phenol is obtained in the form of a slightly green solid.

$^1$H NMR (CDCl$_3$): 3.12 (s, 3H); 5.32-5.33 (m, 1H); 6.58 (d, 1H, J=7.9 Hz); 6.79-6.83 (m, 1H); 6.87 (d, 1H, J=7.4 Hz); 7.3 (d, 1H, J=6.6 Hz); 7.5 (t, 1H, J=7.2 Hz); 8.56 (s, 1H).

Example 25

2-[(6-Methoxypyridin-2-ylamino)methyl]-6-methylphenol

Synthesis According to Scheme 1, Method 1c 80 mg (2.1 mmol, 6 eq) of lithium aluminium hydride are added in small fractions to a mixture of 90 mg (0.35 mmol) of 2-hydroxy-N-(6-methoxypyridin-2-yl)-3-methylbenzamide in 10 ml of dioxane. The reaction medium is heated at 80° C. for 16 h. 80 mg (2.1 mmol, 6 eq) of lithium aluminium hydride are added again and the medium is heated at 80° C. for 4 h. The reaction medium is diluted with 50 ml of ethyl acetate and washed with 50 ml of a saturated solution of ammonium chloride, and then twice with 50 ml of water. The organic phase is dried over magnesium sulphate, filtered and concentrated to dryness. The residue is purified by chromatography over silica, eluting with a heptane/ethyl acetate (1/1) mixture.

2-[(6-methoxypyridin-2-ylamino)methyl]-6-methylphenol is obtained in the form of a white solid.
$^1$H NMR (CDCl$_3$): 2.19 (s, 3H); 3.89 (s, 3H); 4.46 (d, 2H, J=6.7 Hz); 4.75 (s, 1H); 5.93-5.97 (m, 2H); 6.68 (t, 1H, J=7.4 Hz); 6.92 (d, 1H, J=7.5 Hz); 7.0 (d, 1H, J=7.4 Hz); 7.27 (t, 1H, J=7.9 Hz), 9.66 (s, 1H).

Preparation of the 2-hydroxy-N-(6-methoxypyridin-2-yl)-3-methylbenzamide intermediate 10 ml of thionyl chloride are added to 1.47 g (16.11 mmol) of 2-hydroxy-3-methylbenzoic acid and the reaction mixture is heated at 90° C. for 2 h. The reaction medium is concentrated to dryness by azeotroping with toluene. The residue is then put into solution in 10 ml of pyridine, to which 600 mg (4.83 mmol, 1 eq) of 2 methoxypyridin-6-amine are added dropwise, and the reaction medium is left stirring at room temperature for 1 h 30 mins. 30 ml of 1M sodium hydroxide (19.34 mmol, 4 eq) are added and the reaction medium is heated at 60° C. for 16 h. The reaction medium is diluted with 100 ml of ethyl acetate, the aqueous phase is extracted and washed with 50 ml of ethyl acetate. The aqueous phase is then acidified at 0° C. with 37% HCl dropwise to pH=4. The organic phases are extracted twice with 50 ml of ethyl acetate and then they are washed twice with 50 ml of water. The organic phases are concentrated to dryness and the residue is purified by chromatography over silica, eluting with a heptane/ethyl acetate (1/1) mixture.

2-Hydroxy-N-(6-methoxypyridin-2-yl)-3-methylbenzamide is obtained in the form of a white solid.

$^1$H NMR (CDCl$_3$): 2.23 (s, 3H); 3.84 (s, 3H); 6.48 (d, 1H, J=8 Hz); 6.78 (t, 1H, J=7.7 Hz); 7.26 (d, 1H, J=7.3 Hz); 7.38 (d, 1H, J=8 Hz); 7.58 (t, 1H, J=8 Hz); 7.76 (d, 1H, J=7.7 Hz); 8.31 (s, 1H); 12.12 (s, 1H).

All the NMR (nuclear magnetic resonance) spectra are in agreement with the proposed structures. The chemical shifts are expressed in parts per million. The internal reference is tetramethylsilane. The following abbreviations are used: CDCl$_3$=deuterated chloroform, DMSO=deuterated dimethyl sulphoxide, CD$_3$OD=deuterated methanol.

Example 26

Biological Tests

The compounds according to the invention show inhibitory properties on receptors of AR type. This AR receptor-inhibiting activity is measured in a transactivation test through the KdR (resting), KdA (active) and Kdapp (apparent) dissociation constants according to the method set out in *J. Molecular Biology* (1965), 12(1), 88-118, Monod J. et al.

The expression "AR-type receptor inhibitor" means, according to the invention, any compound which has a Kdapp dissociation constant of less than or equal to 1 µM, and a KdR/KdA ratio 10, in a transactivation test.

The preferred compounds of the present invention have a dissociation constant of less than or equal to 500 nM and advantageously less than or equal to 100 nM.

The transactivation test is carried out in the PALM (PC3 Androgen receptor Luciferse MMTV) cell line which is a stable transfectant containing the PMMTV-neo-Luc (reporter gene) and pSG5puro-AR plasmids.

In this study, the affinity of each product for the 2 receptor states (KdR and KdA) is determined, as is an apparent Kd (KdApp). This constant is a result of the 2 Kd, but also depends on the initial equilibrium of the receptor between the active state and the resting state (L$_0$) and on its expression level. It is determined by means of the following formula:

$$1/KdApp=(L0/(1+L0))\times(1/KdR)+(1/(1+L0))\times(1/KdA)$$

To determine these constants, "cross curves" of the test product against a reference agonist, methyltrienolone, are produced in 96-well plates. The test product is used at 10 concentrations and the reference agonist at 7 concentrations.

By way of illustration, a Kdapp of 40 nM is obtained for the compound (1), a Kdapp of 2 nM is obtained for the compound (2), a Kdapp of 8 nM is obtained for the compound (19), a Kdapp of 1000 nM is obtained for the compound (18) and a Kdapp of 200 nM is obtained for the compound (4).

The invention claimed is:

1. A method of preparing a compound of formula (I):

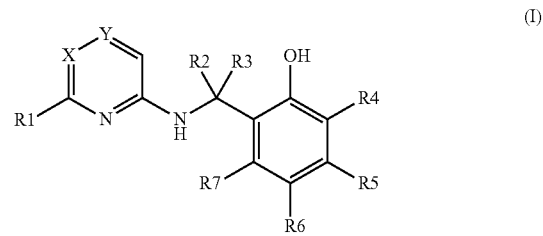

in which:

R$_1$ represents a C$_{2-6}$ alkyl, C$_{3-7}$ cycloalkyl, C$_{1-6}$ alkyloxy, —S(O)$_m$—C$_{1-8}$ alkyl, C$_{1-6}$ fluoroalkyl, C$_{1-6}$ fluoroalkyloxy, —(CH$_2$)$_n$—C$_{3-9}$ cycloalkyl, —(CH$_2$)$_n$—C$_{3-9}$ cycloalkyl, C$_{2-6}$ alkyl-OH, —(CH$_2$)$_n$—C$_{1-8}$ alkyloxy, —(CH$_2$)$_n$—C$_{1-6}$ fluoroalkyl, —(CH$_2$)$_p$—O—C$_{1-6}$ fluoroalkyl, COR$_a$, CN, NO$_2$ or NR$_8$R$_9$ group, a halogen or a phenyl or heteroaryl group comprising either a) from 1 to 4 nitrogen atoms or b) an oxygen or sulphur atom and 1 or 2 nitrogen atom(s); wherein the phenyl and heteroaryl groups can optionally be substituted with one to three identical or different R$_b$ groups, R$_2$ and R$_3$ are identical or different and represent a hydrogen atom or a C$_{1-9}$ alkyl, C$_{3-9}$ cycloalkyl, C$_{1-6}$ fluoroalkyl, —(CH$_2$)$_r$—C$_{3-9}$ cycloalkyl, —C$_{2-6}$ alkyl-OH, —(CH$_2$)$_r$—C$_{1-6}$ alkyloxy, —(CH$_2$)$_r$—C$_{3-7}$ cycloalkyl, —(CH$_2$)$_r$—C$_{1-6}$ fluoroalkyl, or —(CH$_2$)$_q$—O—C$_{1-6}$ fluoroalkyl group, optionally, the R$_2$ and R$_3$ groups can form, with the carbon atom which bears them, a C$_{3-9}$ cycloalkyl group or a heterocycle, R$_4$, R$_5$, R$_6$, R$_7$ are identical or different and represent either a hydrogen atom or a C$_{1-6}$ alkyl, C$_{3-7}$ cycloalkyl, C$_{1-6}$ alkyloxy, —S(O)$_s$—C$_{1-6}$ alkyl, C$_{1-6}$ fluoroalkyl, C$_{1-6}$ fluoroalkyloxy, —(CH$_2$)$_t$—C$_{3-9}$ cycloalkyl, —(CH$_2$)$_t$—C$_{3-9}$ cycloalkyl, —C$_{1-6}$ alkyl-OH, —(CH$_2$)$_t$—C$_{1-6}$ alkyloxy, —(CH$_2$)$_t$—C$_{1-6}$ fluoroalkyl, —(CH$_2$)$_u$—O—C$_{1-6}$ fluoroalkyl, COR$_d$, CN or NR$_8$R$_9$ group, or a halogen or a phenyl or heteroaryl group comprising either a) from 1 to 4 nitrogen atoms or b) an oxygen or sulphur atom and 1 or 2 nitrogen atom(s); these phenyl and heteroaryl groups can optionally be substituted with one to three identical or different R$_c$ groups, X represents CH or N;

Y represents either a nitrogen atom, or a carbon atom substituted with a C$_{1-6}$ alkyl, C$_{3-7}$ cycloalkyl, C$_{1-6}$ alkyloxy, —S(O)$_v$—C$_{1-6}$ alkyl, C$_{1-6}$ fluoroalkyl, C$_{1-6}$ fluoroalkyloxy, —(CH$_2$)$_f$—C$_{3-9}$ cycloalkyl, —(CH$_2$)$_f$—C$_{3-9}$ cycloalkyl, C$_{1-6}$ alkyl-OH, —(CH$_2$)$_f$—C$_{1-6}$ alkyloxy, —(CH$_2$)$_f$—C$_{1-6}$ fluoroalkyl, —(CH$_2$)$_w$—O—C$_{1-6}$ fluoroalkyl, COR$_8$, CN, NR$_{10}$R$_{11}$ or NO$_2$ group, a hydrogen atom or a halogen or a phenyl or heteroaryl group comprising either a) from 1 to 4 nitrogen atoms or b) an oxygen or sulphur atom and 1 or 2 nitrogen atom(s); these phenyl and heteroaryl groups can optionally be substituted with one to three identical or different R$_b$ groups, R$_a$, R$_d$ and R$_e$ are identical or different and represent a C$_{1-6}$ alkyl, C$_{1-6}$ alkyloxy or NR$_{12}$R$_{13}$ group;

$R_b$ and $R_c$ are identical or different and represent a halogen, or a $C_{1-6}$ alkyl, $C_{3-7}$ cycloalkyl, $C_{1-6}$ alkyloxy, —S(O)$_i$—$C_{1-6}$ alkyl, $C_{1-6}$ fluoroalkyl, $C_{1-6}$ fluoroalkyloxy, —(CH$_2$)$_i$—$C_{3-7}$ cycloalkyl, OH, —(CH$_2$)$_i$—$C_{3-7}$ cycloalkyl, $C_{1-6}$ alkyl-OH, —(CH$_2$)$_i$—$C_{1-6}$ alkyloxy, fluoroalkyl, —(CH$_2$)$_z$—O—$C_{1-6}$ fluoroalkyl, COR$_a$, CN or NR$_{14}$R$_{15}$ group;

$R_8$ and $R_{8'}$ are identical or different and represent a $C_{1-6}$ alkyl, $C_{3-7}$ cycloalkyl, —(CH$_2$)$_f$—$C_{3-7}$ cycloalkyl or —(CH$_2$)$_f$—$C_{1-6}$ fluoroalkyl group;

$R_9$, $R_{9'}$, $R_{10}$, $R_{11}$, $R_{12}$, $R_{13}$, $R_{14}$ and $R_{15}$ are identical or different and represent a hydrogen atom or a $C_{1-6}$ alkyl, $C_{3-7}$ cycloalkyl, —(CH$_2$)$_g$—$C_{3-7}$ cycloalkyl or —(CH$_2$)$_g$—$C_{1-6}$ fluoroalkyl group;

optionally, the $R_8$ and $R_9$ groups can form, with the nitrogen atom which bears them, a heterocycle;

optionally, the $R_{8'}$ and $R_{9'}$ groups can form, with the nitrogen atom which bears them, a heterocycle;

optionally, the $R_{10}$ and $R_{11}$ groups can form, with the nitrogen atom which bears them, a heterocycle;

optionally, the $R_{12}$ and $R_{13}$ groups can form, with the nitrogen atom which bears them, a heterocycle;

optionally, the $R_{14}$ and $R_{15}$ groups can form, with the nitrogen atom which bears them, a heterocycle;

f, g, i, l, n, r and t are different or identical and are equal to 1, 2 or 3;

j, m, s and v are different or identical and are equal to 0, 1 or 2;

p, q, u, w and z are different or identical and are equal to 2, 3 or 4;

and also a pharmaceutically acceptable salt, solvate, hydrate, conformer or rotamer thereof, the method comprising:

(a) reacting an aldehyde (II) or a benzyl ketone (II) with an amine (III) in the presence of a reducing agent;

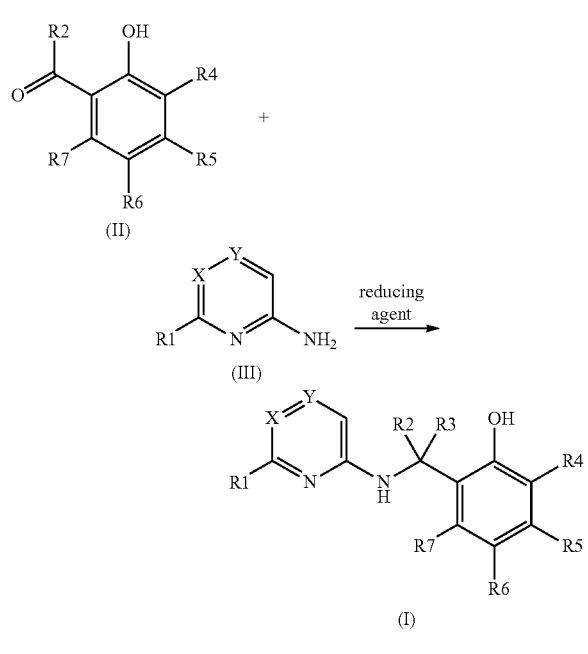

(b) reacting a benzyl amine (VI) with a heterocycle (V) in the presence of a base; or

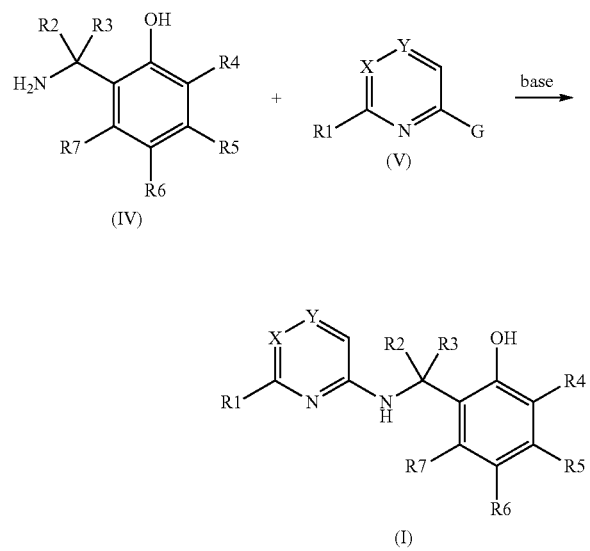

(c) reacting an amide intermediate (VII) with a reactive hydrogen donor

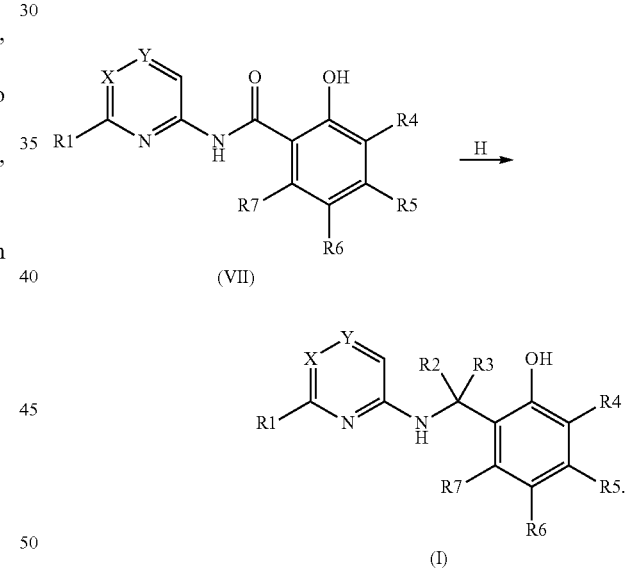

2. The method according to claim 1, wherein the amide intermediate (VII) is prepared by reacting an acyl chloride (VI) with an amine (III)

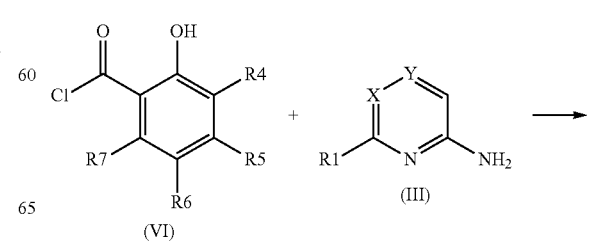

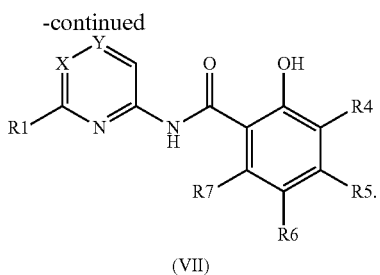

(VII)

3. The method according to claim 1, wherein the reducing agent is sodium triacetoxyborohydride.

4. The method according to claim 1, wherein the base is 1,8-diazabicyclo[5.4.0]undec-7-ene.

5. The method according to claim 1, wherein the reactive hydrogen donor is lithium aluminum anhydride.

6. The method according to claim 1, wherein X represents a carbon atom and Y represents a carbon atom optionally substituted with one of the groups as defined in claim 1.

7. The method according to claim 6, wherein Y represents a carbon substituted with a member selected from the group consisting of a methyl, ethyl, isopropyl, cyclopropyl, $CF_3$, $CONH_2$, $CO_2CH_3$, $CO_2CH_2CH_3$, CN, $NO_2$, $SCH_3$ or $SCH_2CH_3$ group, a hydrogen atom, a halogen, a $OCF_3$, $OCH_3$, $OCH_2CH_3$ or $OCH(CH_3)_2$ group.

8. The method according to claim 1, wherein R1 represents a halogen, an ethyl, an isopropyl, a trifluoromethyl, a nitrile, a nitro, a methoxy, an ethoxy, an isopropoxy, a thiomethyl, a thioethyl or a thioisopropyl group.

9. The method according to claim 8, wherein R1 represents a halogen, a methoxy, an ethoxy, a thiomethyl, a thioethyl or a trifluoromethyl group.

10. The method according to claim 1, wherein the R2 and R3 groups can form tetrahydrofuran, tetrahydropyran, tetrahydrothiopyran, tetrahydro-1-oxythiopyran or tetrahydro-1,1-dioxythiopyran.

11. The method according to claim 1, wherein the R8 and R9 groups can form azetidine, pyrrolidine, piperidine, azepane, morpholine or piperazine.

12. The method according to claim 1, wherein the R10 and R11 groups can form azetidine, pyrrolidine, piperidine, azepane, morpholine or piperazine.

13. The method according to claim 1, wherein the R12 and R13 groups can form azetidine, pyrrolidine, piperidine, azepane, morpholine or piperazine.

14. The method according to claim 1, wherein the R14 and R15 groups can form azetidine, pyrrolidine, piperidine, azepane, morpholine or piperazine.

15. The method according to claim 1, wherein the compound is selected from the group consisting of:
2-[(6-Methoxypyridin-2-ylamino)methyl]phenol;
2-[(6-Bromopyridin-2-ylamino)methyl]phenol;
2[(6-Bromopyridin-2-ylamino)methyl]-4-fluorophenol;
6-(2-Hydroxybenzylamino)pyridine-2-carbonitrile;
2-[1-(6-Methoxypyridin-2-ylamino)ethyl]phenol;
2-[(6-Trifluoromethylpyridin-2-ylamino)methyl]phenol;
2-[(6-Chloropyridin-2-ylamino)methyl]phenol;
2-[(6-Ethylpyridin-2-ylamino)methyl]phenol;
2-[(6-Ethoxypyridin-2-ylamino)methyl]phenol;
2[(6-Isopropoxypyridin-2-ylamino)methyl]phenol;
5-Chloro-2-[(6-methoxypyridin-2-ylamino)methyl]phenol;
2[(2-Trifluoromethylpyrimidin-4-ylamino)methyl]phenol;
2-[(6-Bromopyrazin-2-ylamino)methyl]phenol;
2-[(2-Chloropyrimidin-4-ylamino)methyl]phenol;
2-[(2-Bromopyrimidin-4-ylamino)methyl]phenol;
2-[(2-Chloro-6-methylpyrimidin-4-ylamino)methyl]phenol;
2-[(6-Chloro-4-trifluoromethylpyridin-2-ylamino)methyl]phenol;
2-[(6-Chloro-4-methylpyridin-2-ylamino)methyl]phenol;
2-[(6-Methoxypyrazin-2-ylamino)methyl]phenol;
2-[(2-Methoxypyrimidin-4-ylamino)methyl]phenol;
2-[(2-Methoxy-6-methylpyrimidin-4-ylamino)methyl]phenol;
2-[(6-Methylsulphanylpyridin-2-ylamino)methyl]phenol;
2-[(6-Methanesulphinylpyridin-2-ylamino)methyl]phenol;
2-[(6-Methanesulphonylpyridin-2-ylamino)methyl]phenol;
2-[(6-Methoxypyridin-2-ylamino)methyl]-6-methylphenol;
2-[(4-Bromo-6-methoxypyridin-2-ylamino)methyl]phenol;
2[(6-Bromo-2-methoxypyrimidin-4-ylamino)methyl]phenol;
2-[(4-Chloro-6-methoxypyridin-2-ylamino)methyl]phenol;
2[(6-Bromo-2-methoxypyrimidin-4-ylamino)methyl]phenol;
2-[(4-Bromo-6-methoxypyridin-2-ylamino)methyl]-6-fluorophenol;
2[(4-Bromo-6-methoxypyridin-2-ylamino)methyl]-5-fluorophenol;
2-[(4-Bromo-6-methoxypyridin-2-ylamino)methyl]-3-fluorophenol;
2[(4-Bromo-6-methoxypyridin-2-ylamino)methyl]-4-fluorophenol;
2-[(6-Bromo-2-methoxypyrimidin-4-ylamino)methyl]-4-fluorophenol;
2-[(4-Chloro-6-methoxypyridin-2-ylamino)methyl]-4-fluorophenol;
2-[(6-Chloro-2-methoxypyrimidin-4-ylamino)methyl]-4-fluorophenol;
2-[1-(4-Bromo-6-methoxypyridin-2-ylamino)ethyl]phenol;
2-[1-(4-Bromo-6-methoxypyridin-2-ylamino)propyl]phenol;
2-[1-(6-Bromo-4-methylpyridin-2-ylamino)-1-methylethyl]phenol;
2-[1-(4-Bromo-6-methoxypyridin-2-ylamino)propyl]-4-fluorophenol;
2-[1-(6-Bromopyridin-2-ylamino)propyl]-4-fluorophenol;
4-Fluoro-2-[(6-methoxypyridin-2-ylamino)methyl]phenol;
4-Fluoro-2-[1-(6-methoxypyridin-2-ylamino)ethyl]phenol;
4-Fluoro-2-[1-(6-methoxypyridin-2-ylamino)propyl]phenol;
2-[(6-Bromo-4-methoxypyridin-2-ylamino)methyl]phenol;
2-[(6-Bromo-4-methylpyridin-2-ylamino)methyl]phenol; and
-[(6-Chloro-4-methoxypyridin-2-ylamino)methyl]phenol
and a pharmaceutically acceptable salt, solvate, hydrate or rotamer thereof.

* * * * *